US008064999B2

(12) United States Patent
Jackson et al.

(10) Patent No.: US 8,064,999 B2
(45) Date of Patent: Nov. 22, 2011

(54) DISTANCE-BASED ANALYSIS OF RETURN CYCLES FOR TACHYCARDIA DISCRIMINATION

(75) Inventors: Troy E. Jackson, New Brighton, MN (US); Paul A. Belk, Maple Grove, MN (US); Mark L. Brown, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 469 days.

(21) Appl. No.: 12/362,548

(22) Filed: Jan. 30, 2009

(65) Prior Publication Data

US 2010/0198290 A1 Aug. 5, 2010

(51) Int. Cl.
*A61N 1/00* (2006.01)
(52) U.S. Cl. .......................................... 607/9
(58) Field of Classification Search .................. 607/9
See application file for complete search history.

(56) References Cited

U.S. PATENT DOCUMENTS

| | | | |
|---|---|---|---|
| 4,312,356 A | 1/1982 | Sowton et al. | |
| 5,978,707 A * | 11/1999 | Krig et al. .................. | 607/14 |
| 7,149,577 B2 | 12/2006 | Sharma et al. | |
| 7,317,942 B2 | 1/2008 | Brown | |
| 7,392,082 B2 | 6/2008 | Sharma | |
| 2004/0106956 A1 | 6/2004 | Sharma et al. | |
| 2005/0251217 A1 | 11/2005 | Brown | |
| 2006/0224195 A1 | 10/2006 | Sharma | |
| 2007/0191897 A1 | 8/2007 | Belk et al. | |
| 2007/0191900 A1 | 8/2007 | Belk et al. | |

FOREIGN PATENT DOCUMENTS
EP 0597459 B1 10/1999

OTHER PUBLICATIONS

P0029638.01 (PCT/US2010/020697) PCT Notification of Transmittal of the International Search Report and the Written Opinion of the International Searching Authority, dated Mar. 22, 2010, 10 pages.
Waldo Al, "Atrial Flutter Entrainment Characteristics", J. Cardiovasc. Electrophysiol., Mar. 1997, pp. 337-352, vol. 8.
Callans DJ, et al. "Characterization of Return Cycle Responses Predictive of Successful Pacing-Mediated Termination of Ventricular Tachycardia", J Am Coll Cardiol, 1995, pp. 47-53, vol. 25.
Arenal A, et al. "Differentiation of ventricular and supraventricular tachycardias based on theanalysis of the first postpacing interval after sequential anti-tachycardia pacing in implantable cardioverter-defibrillator patients" Heart Rhythm, 2007, pp. 316-322, vol. 4.
Arenal A., et al. "First Postpacing interval variability during right ventricular stimulation: A single algorithm for the differential diagnosis of regular tachycardias" 1997, pp. 671-677, vol. 98.
Yee R. et al. "Determination of antitachycardia pacing failure mechanism by return cycle length analysis" World Congress Cardiology 2006, Abstract.

* cited by examiner

*Primary Examiner* — George Manuel
(74) *Attorney, Agent, or Firm* — Michael C. Soldner

(57) ABSTRACT

A medical device and associated method classify a tachycardia according to a site of origin of the tachycardia. Cardiac signals are sensed and a tachycardia event is detected in response to the sensed cardiac signals. Pacing pulses are delivered and a time interval corresponding to a distance traversed by a depolarization associated with the last one of the pacing pulses from a site of delivery of the plurality of pacing pulses is determined. The tachycardia event is classified according to a site of origin in response to the determined time interval.

20 Claims, 9 Drawing Sheets

US 8,064,999 B2

DISTANCE-BASED ANALYSIS OF RETURN CYCLES FOR TACHYCARDIA DISCRIMINATION

TECHNICAL FIELD

The disclosure relates generally to implantable medical devices and, in particular, to a method and apparatus for discriminating arrhythmias.

BACKGROUND

A typical implantable pacemaker/cardioverter/defibrillator (PCD) device has the capability of providing a variety of anti-tachycardia pacing (ATP) regimens. Normally, these regimens are applied according to a pre-programmed sequence, and each regimen includes a predetermined number of pacing pulses. After the series of pacing pulses is delivered, the device checks to determine whether the series of pulses was effective in terminating the detected tachycardia. Typically, termination is confirmed by a return to either a sinus rhythm or demand-paced rhythm, in which successive spontaneous depolarizations are separated by at least a defined interval. If the tachycardia is not terminated, the PCD device may deliver a subsequent series of pacing pulses having modified pulse parameters, e.g. reduced inter-pulse intervals and/or an altered number of pulses. When ATP attempts fail to terminate the tachycardia, high-voltage cardioversion shocks may be delivered. Since shocks can be painful to the patient and consume relatively greater battery charge than pacing pulses, it is desirable to avoid delivering unnecessary shocks.

The success of a tachycardia therapy depends in part on the accuracy of the tachycardia detection. In some cases, a tachycardia originating in the atria, i.e. a supraventricular tachycardia (SVT), is difficult to distinguish from a tachycardia originating in the ventricles, i.e. a ventricular tachycardia (VT). For example, both the atrial chambers and the ventricular chambers may exhibit a similar tachycardia cycle length when an SVT is conducted to the ventricles or a VT is conducted retrograde to the atria. Accordingly, methods are needed for accurately classifying a detected tachycardia as VT or SVT to allow the most appropriate therapy to be delivered by the PCD, with the highest likelihood of success and without unacceptably delaying attempts at terminating the tachycardia.

DETAILED DESCRIPTION

Figure 1:
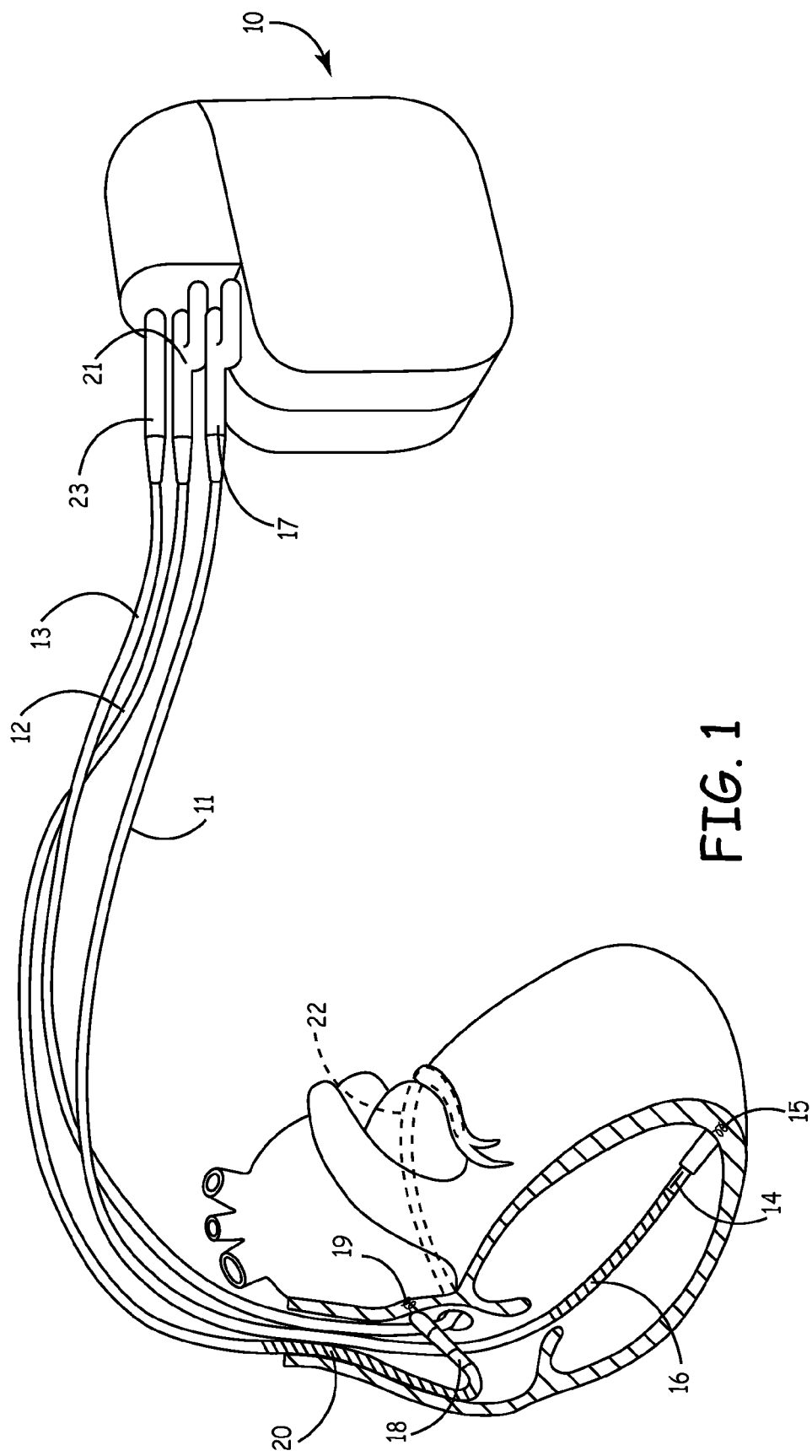
FIG. 1 shows a PCD device, right ventricular lead, atrial/SVC lead, and coronary sinus lead.

In the following description, references are made to illustrative embodiments. It is understood that other embodiments may be utilized without departing from the scope of the invention. For purposes of clarity, the same reference numbers are used in the drawings to identify similar elements.

FIG. 1 shows pacemaker/cardioverter/defibrillator PCD device 10, right ventricular lead 11, atrial/SVC lead 12, and coronary sinus lead 13. PCD device 10 delivers electrical pulses for anti-tachycardia pacing (ATP) therapy, cardioversion, and defibrillation through leads 11-13. In various embodiments, device 10 provides tachycardia discrimination based upon an analysis of a distance traversed by an ATP polarization. The distance analysis includes measuring a return cycle length (RCL) at the end of a preceding train of ATP pulses. ATP therapy may be used to terminate tachycardia located in either the atrial or ventricular regions of the heart. Tachycardia discrimination methods described herein relate primarily to measuring a return cycle length in a ventricle for discriminating SVT and VT. However, an ATP therapy may be delivered in an atrial chamber and the corresponding return cycle length may be measured to enable distance-based SVT and VT discrimination.

Located adjacent the distal end of right ventricular lead 11 are ring electrode 14, tip electrode 15, and elongated coil electrode 16. At the proximal end of right ventricular lead 11 is a bifurcated connection 17, which connects electrodes 14, 15, and 16 to circuitry within device 10. Electrodes 14 and 15 are used to deliver ventricular anti-tachycardia pacing (ATP) pulses, and for sensing ventricular depolarizations or R-waves, while electrode 16 is used to deliver defibrillation or cardioversion shocks.

Atrial/SVC lead 12 also includes three electrodes 18-20. Located adjacent the J-shaped distal end of atrial lead 12 are a second ring electrode 18 and tip electrode 19. Located proximal to ring electrode 18 is elongated coil electrode 20. At the proximal end of atrial/SVC lead 12 is bifurcated connection 21, which connects electrodes 18,19 and 20 to circuitry within PCD device 10.

Electrodes 18 and 19 are used to deliver atrial ATP pulses and for sensing atrial depolarizations or P-waves, while electrode 20 is used for delivering defibrillation or cardioversion shocks.

Coronary sinus lead 13 includes elongated coiled defibrillation electrode 22. Defibrillation electrode 22, illustrated in FIG. 1 as a broken line, is located within the coronary sinus and great vein of the heart. At the proximal end of coronary sinus lead 13 is connector plug 23, which connects defibrillation electrode 22 to circuitry within PCD device 10.

Other lead configurations and electrode locations may be substituted for the lead set illustrated. For example, in a two lead system, atrial defibrillation and sensing electrodes might be added to either coronary sinus lead 13 or right ventricular lead 11 instead of being located on separate atrial lead 12. In any of the configurations, all leads are connected to circuitry within PCD device 10, which controls delivery of ATP pulses and cardioversion shocks to selected electrodes, and processes depolarizations sensed by the electrodes.

For the sake of simplicity, electrode 15 located at the distal end of right ventricular lead 11 is used to illustrate delivery of ATP therapy throughout this description, although any of the electrodes discussed above are capable of providing ATP therapy. It is usually desirable to apply ATP therapy from an electrode located in the chamber of origin of the tachyarrhythmia. Tachyarrhythmia discrimination methods described herein allow the chamber of origin to be identified following delivery of ATP in either an atrium or a ventricle.

Figure 2:
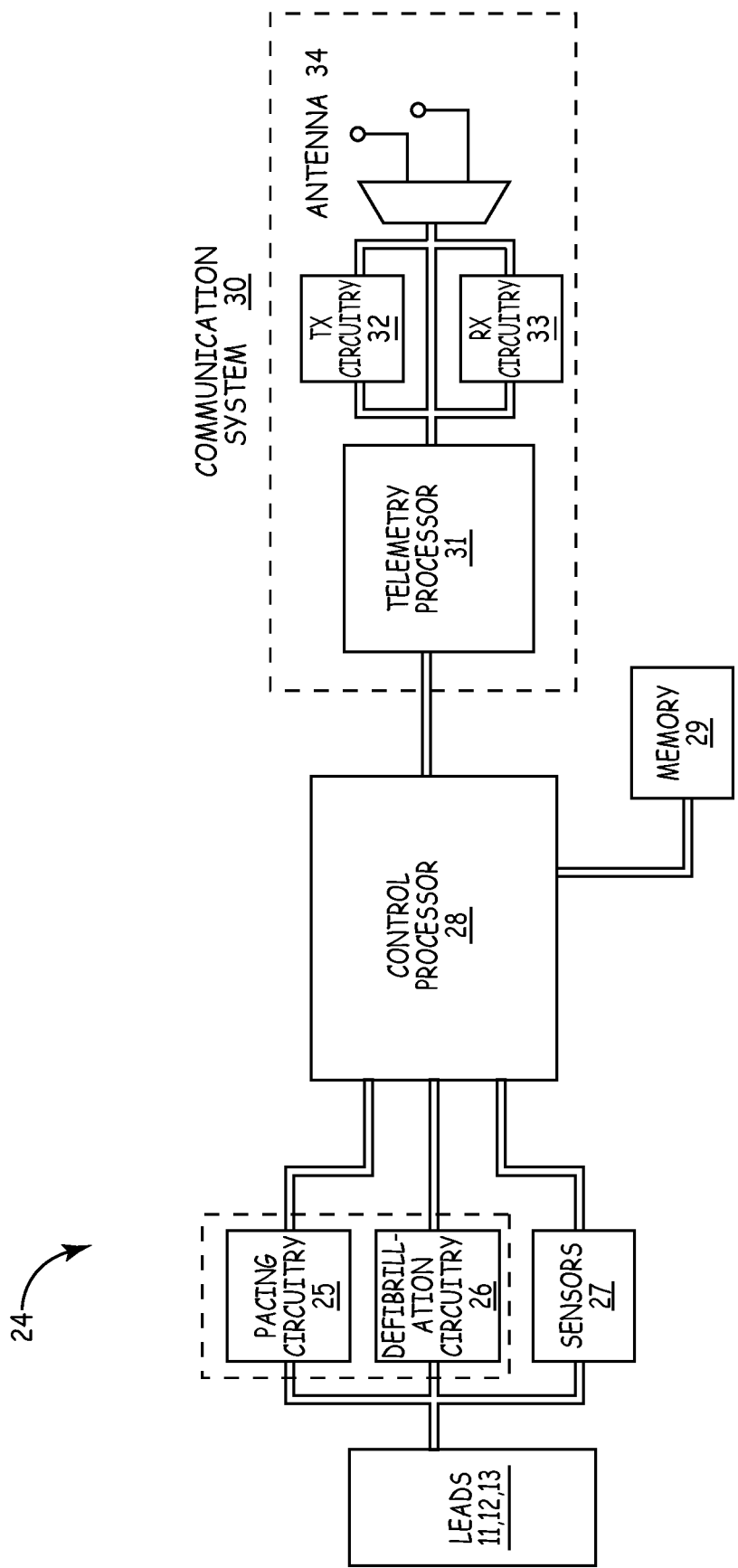
FIG. 2 shows a simplified functional block diagram of circuitry located within the PCD device of FIG. 1.

FIG. 2 shows a simplified functional block diagram of circuitry 24 located within PCD device 10. Circuitry 24 includes pacing circuitry 25, defibrillation circuitry 26, sensor circuitry 27, control processor 28, memory 29, and communication system 30. Leads 11, 12 and 13 are each connected to pacing circuitry 25, defibrillation circuitry 26 and sensor circuitry 27. This is because each lead (and in turn individual electrodes associated with each lead) may be used in multiple capacities to sense depolarizations, deliver anti-tachycardia pacing pulses, and deliver defibrillation or cardioversion shocks. Control processor 28 receives input through sensor circuitry 27 from leads 11, 12 and 13 concerning depolarizations sensed throughout the heart by the number of electrodes connected to leads 11, 12 and 13. Based on input received from sensor circuitry 27, control processor 28 performs calculations to determine the proper course of action, which may include providing ATP therapy to one or more electrodes through pacing circuitry 25, providing defibrillation or cardioversion shocks to one or more electrodes through defibrillation circuitry 26, or providing no treatment at all. Control processor 28 stores selected data to memory 29, and retrieves stored data from memory 29 as necessary. Communication system 30 includes telemetry processor 31, transmission circuitry 32, receiving circuitry 33, and antenna 34. Communication system 30 allows communication between PCD device 10 and devices external to the patient.

Figure 3:
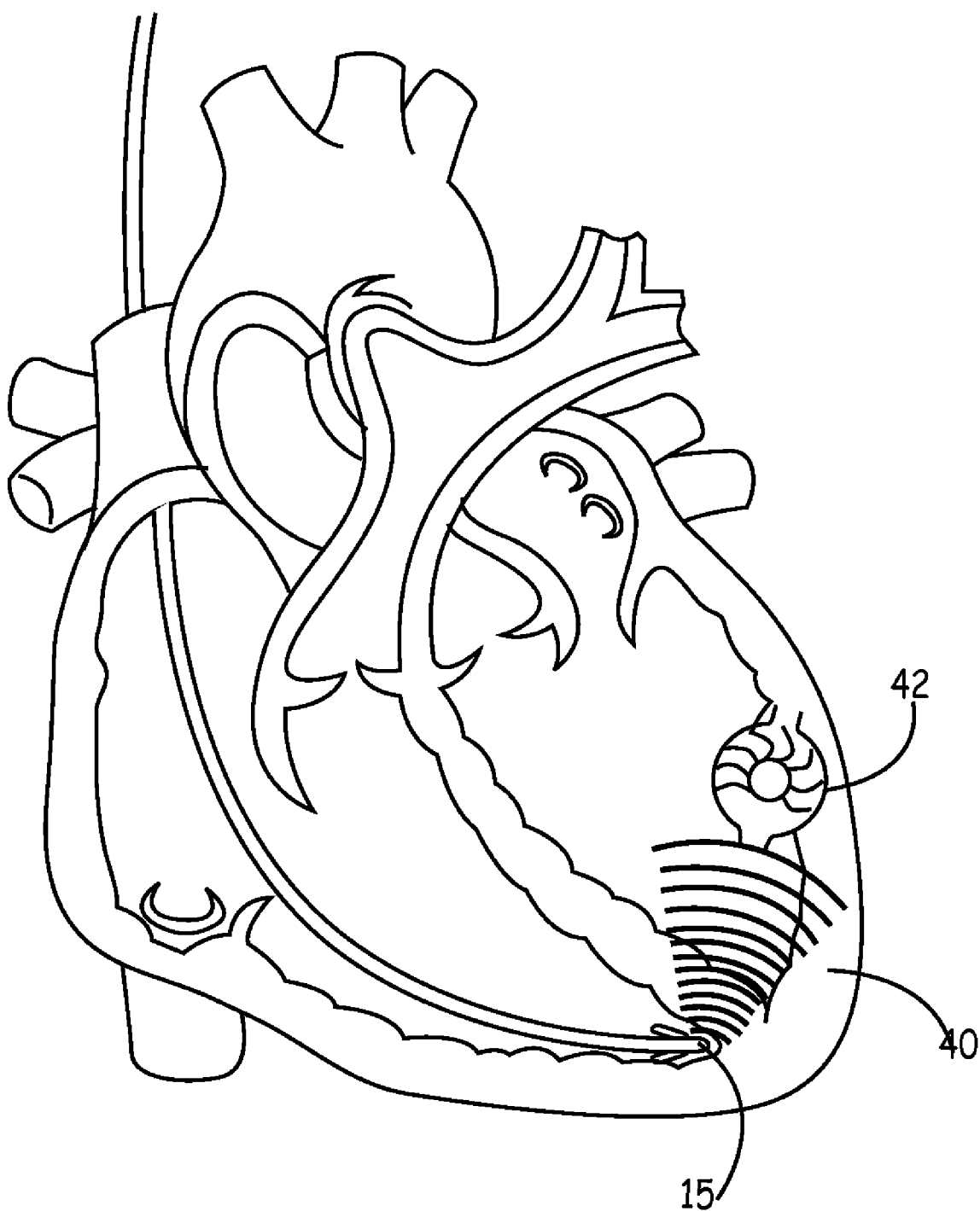
FIG. 3 is a simplified schematic diagram of the delivery of a sequence of ATP pulses to a patient's heart.

FIG. 3 is a simplified schematic diagram of the delivery of a sequence of ATP pulses 40 by PCD device 10 (not shown) to a patient's heart via electrode 15 (as shown in FIG. 1). ATP pulses 40 are delivered in response to detection of a tachycardia event. In the example shown, the tachycardia event is caused by a reentrant tachycardia circuit 42. ATP pulses 40 delivered to electrode 15 radiate outward from electrode 15 towards reentrant tachycardia circuit 42. FIGS. 4A-4E show the propagation of ATP pulses 40 in greater detail.

Figure 4A:
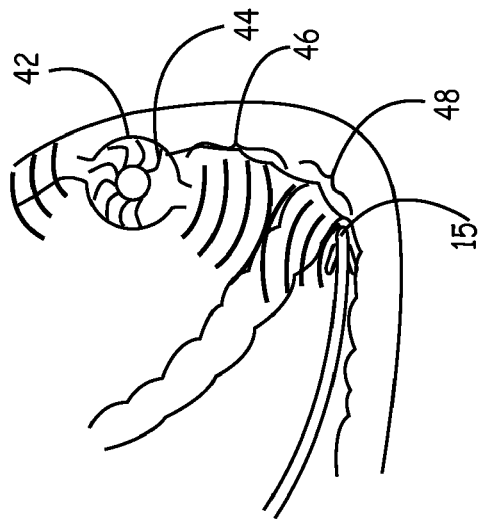
FIGS. 4A-4E are schematic illustrations of treatment of a reentrant tachycardia using ATP therapy.

FIGS. 4A-4E are schematic illustrations of treatment of a reentrant tachycardia using ATP therapy. While embodiments described herein are illustrated using the example of a reentrant ventricular tachycardia, it is recognized that the tachycardia classification and treatment methods described herein may be applied when a ventricular or atrial tachycardia is a reentrant form of tachycardia or a focal form of tachycardia. FIG. 4A shows reentrant tachycardia circuit 42 and reentrant wavefront 44 circling around circuit 42. As reentrant wavefront 44 propagates around reentrant tachycardia circuit 42, a component of reentrant wavefront 44 also radiates outward away from reentrant circuit 42, shown as outward radiating reentrant wavefront 46. Reentrant wavefront 46 radiating away from reentrant circuit 42 is sensed by electrode 15. Sensed depolarizations associated with wavefronts arising from reentrant circuit 42 are utilized by PCD device 10 to determine the presence of a tachycardia event. The tachycardia cycle length (TCL) is a measured interval of time between successive depolarization wavefronts sensed by an electrode during a tachycardia event. While a tachycardia event, which is identified in response to a multiple number of intervals having corresponding cycle lengths less than a predetermined threshold, and may therefore consist of a multiple number of different cycle lengths, the tachycardia event can be assigned a tachycardia cycle length based on a single cycle length measurement associated with one of the multiple cycle lengths, or on an average of the cycle lengths associated with several successive intervals.

Figure 4B:
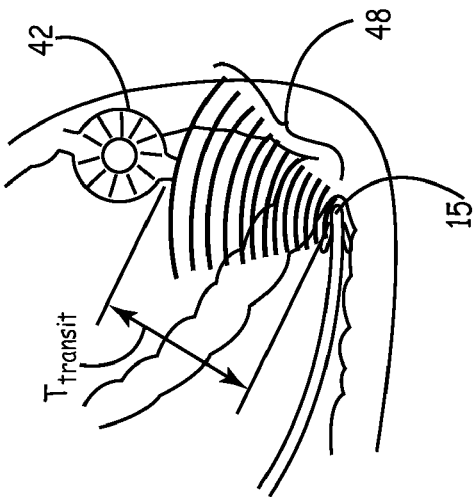

As illustrated in FIG. 4B, PCD device 10 responds to the sensed tachycardia event by delivering ATP therapy, which consists of a number of ATP pulses (a regimen) delivered via electrode 15 at pacing cycle lengths shorter than the TCL. ATP pulses evoke depolarizations 48 radiating away from electrode 15 in all directions, including towards reentrant circuit 42. ATP evoked depolarizations 48 will collide with outward radiating reentrant wavefronts 46 radiating away from reentrant circuit 42, causing a cancellation of both outward radiating reentrant wavefronts 46 and an ATP depolarization 48. By delivering ATP pulses at a rate faster than the pace of outward radiating reentrant wavefronts 46, collisions between ATP depolarizations 48 and outward radiating reentrant wavefronts 46 occur further and further from electrode 15 and closer and closer to reentrant circuit 42.

Figure 4C:
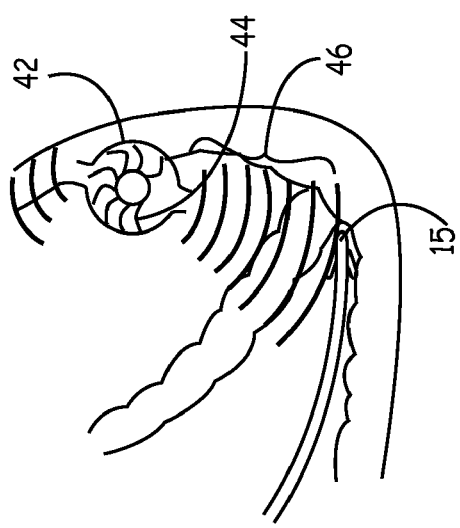
Figure 4D:
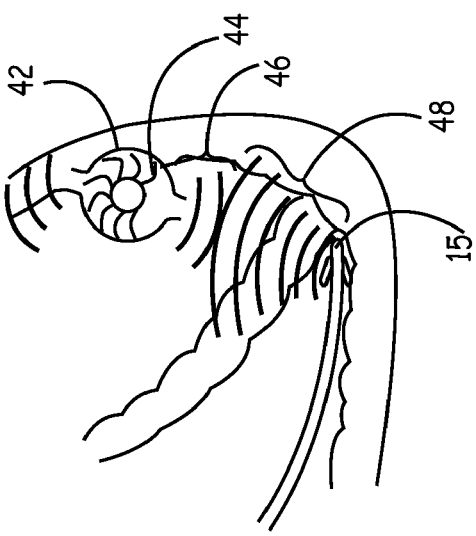

FIGS. 4C and 4D illustrate this point. As ATP pulses are provided at a rate faster than the tachycardia (and therefore faster than the rate of incoming reentrant wavefronts 46), successive ATP depolarizations 48 progress closer and closer to reentrant circuit 42. This process of ATP depolarizations 48 progressing closer and closer to reentrant circuit 42 with each successive ATP pulse is known as "peel back."

Figure 4E:
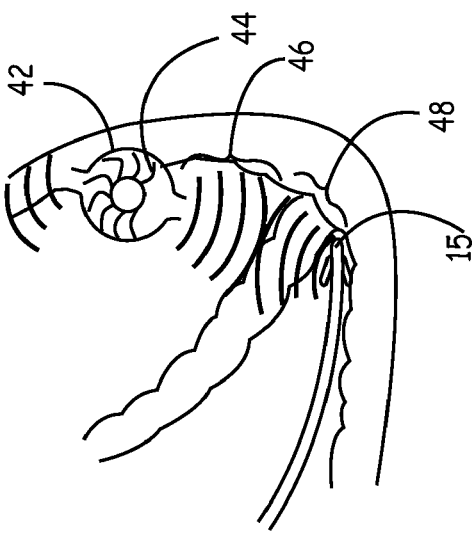

In FIG. 4E, ATP depolarizations 48, approaching reentrant circuit 42 at a rate greater than the rate of the tachycardia event, reach and enter reentrant circuit 42. With the proper timing of the ATP pulses, excitable cardiac tissue within reentrant circuit 42 is depolarized, thus blocking a circulating reentrant wavefront 44 within reentrant circuit 42.

As described in detail below, during delivery of an ATP regimen, tachycardia discrimination methods take into account a transit time 50, which is the amount of time for an ATP depolarization to travel from the pacing site (e.g. electrode 15) to reentrant circuit 42. The transit time 50 thus corresponds to a distance from the electrode 15 to reentrant circuit 42. Analysis of the transit time as a measure of the distance between the electrode 15 and the reentrant circuit 42 allows the chamber of origin of the tachycardia to be identified. If a distance to the tachycardia origin indicated by a computed transit time is greater than a maximum possible distance from a ventricular electrode 15 to any ventricular location, the tachycardia is classified as SVT. If the distance indicated by a computed transit time is less than a maximum distance corresponding to a ventricular location, the tachycardia is classified as VT.

While a distance may be computed from the transit time using a conduction speed of a depolarization wavefront through the myocardium, the transit time may be used directly as a metric of the distance since the conduction speed in the heart may be approximated as a constant. The methods described herein, determine a time interval corresponding to the distance between an electrode delivering ATP and an origin of the tachycardia event. Tachycardia discrimination is based on the determined time interval.

FIGS. 4A-4E illustrate the basics of how ATP depolarizations interact with reentrant tachycardias. In order to be effective in terminating the tachycardia, the ATP therapy regimen must succeed in two objectives. The first objective is to advance the depolarizations 48 created by ATP pulses all the way to the location of reentrant circuit 42. In order to move each successive collision between ATP depolarizations 48 and outward radiating reentrant wavefronts 46 closer and closer to reentrant circuit 42, each ATP pulse provided in a given regimen is provided at a rate, determined by the ATP cycle length, that is faster than the rate of the tachycardia. The ATP cycle length is defined for each ATP pulse in a given regimen as the interval of time from either the last sensed depolarization wavefront (for the first pace of a therapy regimen), or the previous delivered ATP pulse, until the delivery of the next ATP pulse.

The second objective is to eliminate the excitability in reentrant circuit 42 so the reentry process can no longer occur. This is a function of advancing the rate of the tachycardia within reentrant circuit 42 to a rate that cannot be sustained by the reentrant circuit 42.

One reason for ATP therapy to fail is incomplete peel back, e.g., when the number of ATP pulses and/or the ATP cycle lengths are insufficient in achieving complete peel back. Another reason ATP therapy may fail is when ATP is delivered in the ventricle and the detected tachycardia episode is originating in the atria. Accordingly, accurate tachycardia discrimination according to the site of the tachycardia origin is important in selecting the appropriate therapy and successfully terminating the tachycardia.

By attempting delivery of ATP therapy immediately, the tachycardia may be terminated without requiring further discrimination methods. However, when the ATP therapy fails to terminate the tachycardia event, a time interval corresponding to the distance traversed by the last ATP pulse depolarization is useful in determining a site of origin of the tachycardia.

In order to compute transit time 50 illustrated in FIG. 4E, corresponding to the distance traversed by an ATP depolarization, a return cycle length (RCL) is measured. The RCL is the time between delivery of the last pulse of an ATP regimen and the first sensed depolarization subsequent to the ATP. When peel back is complete, the RCL can be thought of as the time for the last ATP pulse depolarization to travel from electrode 15 to reentrant circuit 42, around the reentrant circuit 42, which corresponds to the tachycardia cycle length, and back to electrode 15. Accordingly, the RCL is approximately twice the transit time (TT) 50 (to reentrant circuit 42 and back again) plus the TCL or:

$$RCL = 2TT + TCL. \quad \{1\}$$

Since, the RCL has a dependency on the tachycardia cycle length and the cycle length is often not consistent throughout the duration of a tachycardia, examination of the RCL alone for tachycardia discrimination may not be reliable. As such, tachycardia discrimination methods relying on a measured time interval as a metric of the distance traversed by an ATP polarization, takes into account both a measured RCL and the originally detected tachycardia cycle length (TCL). Equation {1} can be solved for the transit time as:

$$TT = (RCL - TCL)/2 \quad \{2\}$$

wherein the RCL and TCL can each be measured. When peel back is complete, the transit time 50 corresponds to the distance from electrode 15 to the site of origin of the tachycardia event. Thus transit time 50 can be used as a metric of the distance from an electrode to a site of tachycardia origin, and therefore be used to discriminate between SVT and VT.

The factor of 2 in equation {2} can be ignored since it is a constant. In some embodiments, a time interval (TI) corresponding to the distance traversed by an ATP depolarization wavefront from the stimulation electrode may be computed simply as:

$$TI = RCL - TCL. \quad \{3\}$$

The time interval TI will correspond to twice the transit time 50 to the site of origin of the tachycardia when complete peel back occurs. When peel back is incomplete, the time interval TI computed by equation {3} will be less than the transit time 50 and correspond to the distance traversed by the ATP depolarization wavefront toward, but not reaching, the tachycardia origin. As such, when peel back is incomplete, the computed time interval TI corresponds to a minimum limit of the transit time 50, i.e. the transit time 50 must be greater than half of the time interval computed using equation {3}. As will become apparent from the description herein, the time interval TI computed using equation {3}, or any variation thereof that includes a difference between the RCL and the TCL, can be used for classifying a detected tachycardia event according to a site of origin.

Figure 5:
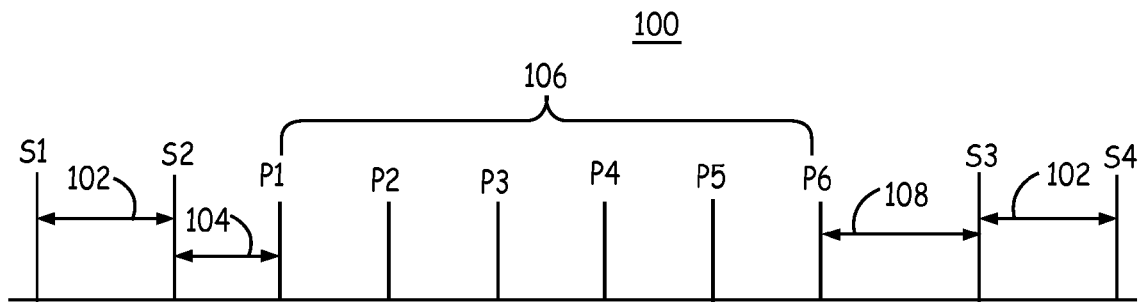
FIG. 5 is a timeline of a delivered ATP therapy.

FIG. 5 is a timeline 100 of a delivered ATP therapy. The S1 and S2 events are sensed depolarizations corresponding to a tachycardia event occurring at a TCL 102. Upon detecting the tachycardia, ATP pulses 106 including pulses P1 through P6, are delivered at an ATP cycle length 104 that is shorter than TCL 102. ATP pulses 106 are shown delivered at a constant cycle length 104. This ATP regimen is referred to as burst ATP. ATP pulses 106 may alternatively be delivered in a ramp regimen in which the ATP cycle length 104 is progressively shortened between pulses 106. ATP pulses 106 may be delivered in any burst, ramp, ramp plus burst, or other ATP regimen.

A return cycle length (RCL) 108 is the time interval following the last pacing pulse P6 and the first sensed event S3 occurring after the last pulse P6. The response to a delivered ATP regimen may be termination of the tachycardia, acceleration of the tachycardia, or a return to tachycardia at the initially-detected tachycardia cycle length 102. As will be described herein, the RCL 108 is measured and used in computing a time interval used for tachycardia discrimination when the tachycardia is not terminated nor accelerated by the ATP therapy.

Figure 6A:
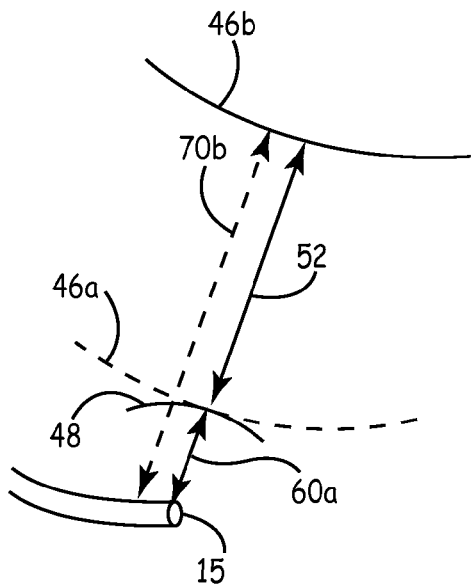
FIGS. 6A and 6B are schematic illustrations of a return cycle length measured when "peel back" is incomplete.
Figure 6B:
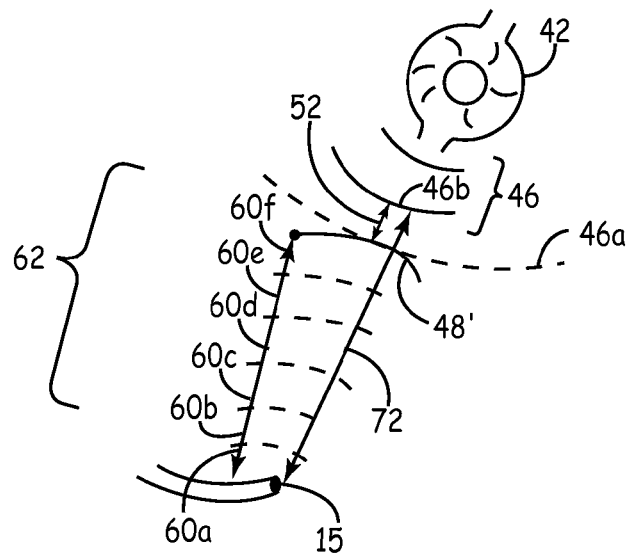

FIGS. 6A and 6B are schematic illustrations of a RCL measured when peel back is incomplete. In this case, a measured RCL will relate to the distance that the ATP depolarizations advance toward the tachycardia site of origin.

Prior to delivering the ATP pulses, tachycardia depolarization wavefronts are sensed at electrode 15 occurring at a TCL 52. In FIG. 6A, a single ATP pulse is delivered. The ATP pulse is delivered at a cycle length shorter than the measured TCL 52. The "prematurity" of an ATP pulse is the difference between that pulse's ATP cycle length and the TCL. For example, if an initial ATP pulse is delivered at a cycle length 20 ms shorter than the TCL, the prematurity for that ATP pulse is 20 ms. In FIG. 6A, the depolarization 48 for an initial ATP pulse will travel a distance 60a from electrode 15 corresponding to one-half the prematurity of the pacing pulse before colliding with the next oncoming tachycardia wavefront 46a. This distance 60a corresponds to approximately one-half of the prematurity of the ATP pulse because the ATP pulse wavefront and the tachycardia wavefront are traveling towards each other at about the same speed.

A RCL measured after the single ATP pulse will be equal to the sum of the time that the ATP wavefront advanced toward wavefront 46a and the time required for the next tachycardia wavefront 46b to travel the distance 70 to reach electrode 15. After cancellation of wavefront 46a, the time required for wavefront 46b to reach electrode 15 will be the TCL 52 and the time required for wavefront 46b to travel back through distance 60a. Stated differently, the RCL will be sum of the prematurity of the ATP pacing pulse (which corresponds to twice the distance 60a) and the TCL 52.

In FIG. 6B, an ATP regimen is delivered including 6 pacing pulses delivered having a total prematurity that advances the final ATP wavefront 48' a distance 62. The total prematurity of the 6 pacing pulses is the sum of the individual prematurites of each pacing pulse. Each of the six pacing pulses in the ATP regimen will travel sequentially longer distances 60a through 60f, respectively, as the cumulative prematurity of the number of pulses delivered increases. The consecutively longer distance 60a through 60f traveled by a given ATP pulse corresponds to half of the cumulative prematurity of all of the pacing pulses delivered up to and including the given ATP pulse. The last ATP depolarization wavefront 48' will travel toward the reentrant circuit 42 a distance 62 corresponding to one half of the total prematurity.

The first depolarization sensed at electrode 15 after delivering the last ATP pulse will correspond to the tachcyardia wavefront 46b following the last tachycardia wavefront 46a that was cancelled by the last delivered ATP depolarization 48'. A RCL measured after the last ATP pulse will therefore be the sum of the distance 62 traveled by the last ATP pulse and the distance 72 traveled by the next tachycardia depolarization 46b to electrode 15 after cancellation of depolarization 46a. The distance 72 is thus the sum of the distance 62 and the distance traveled during TCL 52. Since the distance 62 corresponds to half of the total prematurity of the delivered ATP pulses, the RCL will be equal to the total prematurity of the ATP pulses (twice the distance 62) plus the TCL 52. This RCL measurement during incomplete peel back can be expressed as:

$$RCL = TCL + TP$$

A measurement of RCL that is approximately equal to a measured TCL and the total prematurity is thus an indication of incomplete peelback. The ATP regimen peeled back to a specific distance and did not encounter the tachycardia circuit (or focal site), thus the tachycardia origin must be at a greater distance than the distance traveled by the last pulse of the ATP regimen. The incomplete peelback response thus indicates that the transit time to the tachycardia origin is at least greater than half of the total prematurity of the delivered ATP regimen. Thus, half of the total prematurity of a delivered ATP regimen resulting in incomplete peelback can be referred to as a "lower bound" of the transit time to the tachycardia origin because the tachycardia origin is at least a distance greater than the distance traversed by the last ATP pulse during incomplete peel back.

Figure 7A:
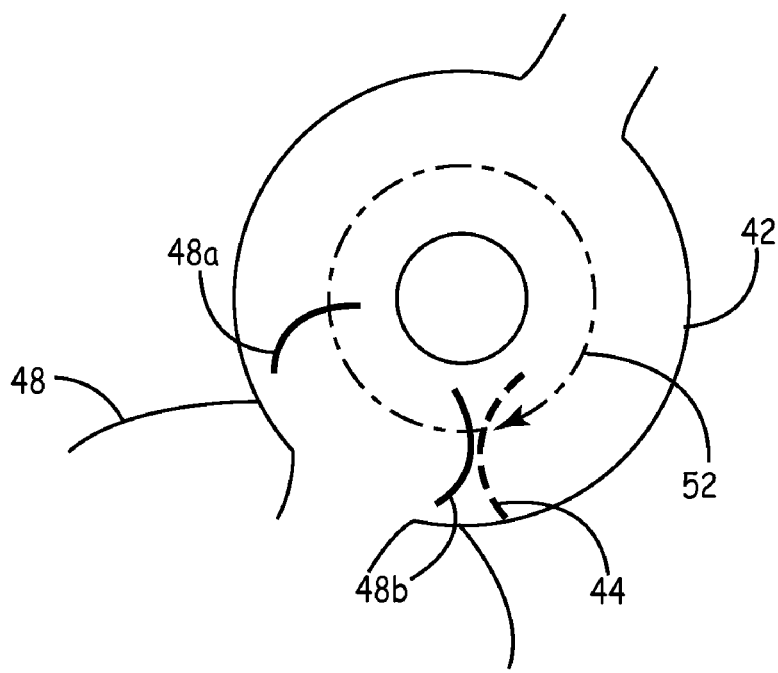
FIG. 7A is a schematic illustration of the concept of "reset" which occurs when peel back is complete.

FIG. 7A is a schematic illustration of the concept of "reset" which occurs when peel back is complete. In FIG. 7A, an ATP depolarization 48 has reached and entered the reentrant circuit 42. The ATP depolarization 48 entering reentrant circuit 42 will travel in both directions, as represented by depolarizations 48a and 48b. For illustration purposes, assume a circulating reentrant wavefront 44 travels in a clockwise direction. The time for a reentrant wavefront 44 to conduct around the circuit is the TCL 52.

The ATP depolarization wavefront 48b, traveling in a counter-clockwise direction, will collide with the oncoming circulating wavefront 44 and the two wavefronts 48b and 44 will cancel each other. When timed appropriately during the TCL, the ATP depolarization wavefront 48a will "jump in line" ahead of the circulating reentrant wavefront 44. This phenomenon can be referred to as "reset" in that the ATP depolarization 48a has altered a cycle length within the tachycardia circuit 42. If depolarization 48 is the final pulse of an ATP regimen, the next depolarization sensed by electrode 15 will be the circulating ATP depolarization 48a after it travels around reentrant circuit 42 and back to electrode 15. When the tachycardia event is not terminated, the next tachycardia wavefront will return at the TCL 52.

Figure 7B:
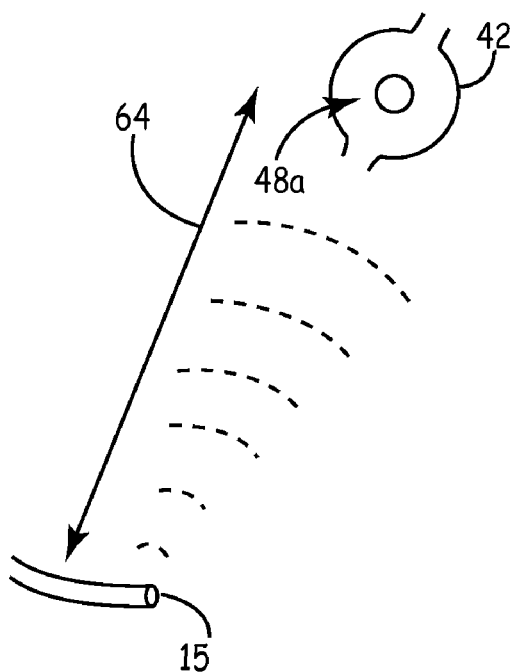
FIG. 7B is a schematic illustration of the return cycle length measured when reset occurs.

FIG. 7B is a schematic illustration of the RCL measured when reset occurs. When peel back is complete, the RCL will be shorter than the sum of the TCL and the total prematurity because the last ATP depolarization 48a has "jumped in line" earlier than the next expected tachycardia wavefront 44. The first depolarization sensed at electrode 15 after the last ATP pulse will correspond to the last ATP depolarization 48a after it has traveled to the reentrant circuit 42 (distance 64), traveled the re-entrant circuit, and returned to electrode 15 (distance 64). The sensed depolarization can be thought of as an "echo" of the last ATP pulse. Since the depolarization 48a is going to travel back toward electrode 15 earlier than the next expected tachycardia wavefront 44 (shown in FIG. 7A) would have, the RCL will be shorter than the total prematurity and the TCL. Accordingly, a measured RCL that is less than the sum of the measured TCL and the TP is an indication of reset. The RCL observed after a reset allows a direct measurement of the transit time as described in equation {2}.

Figure 8:
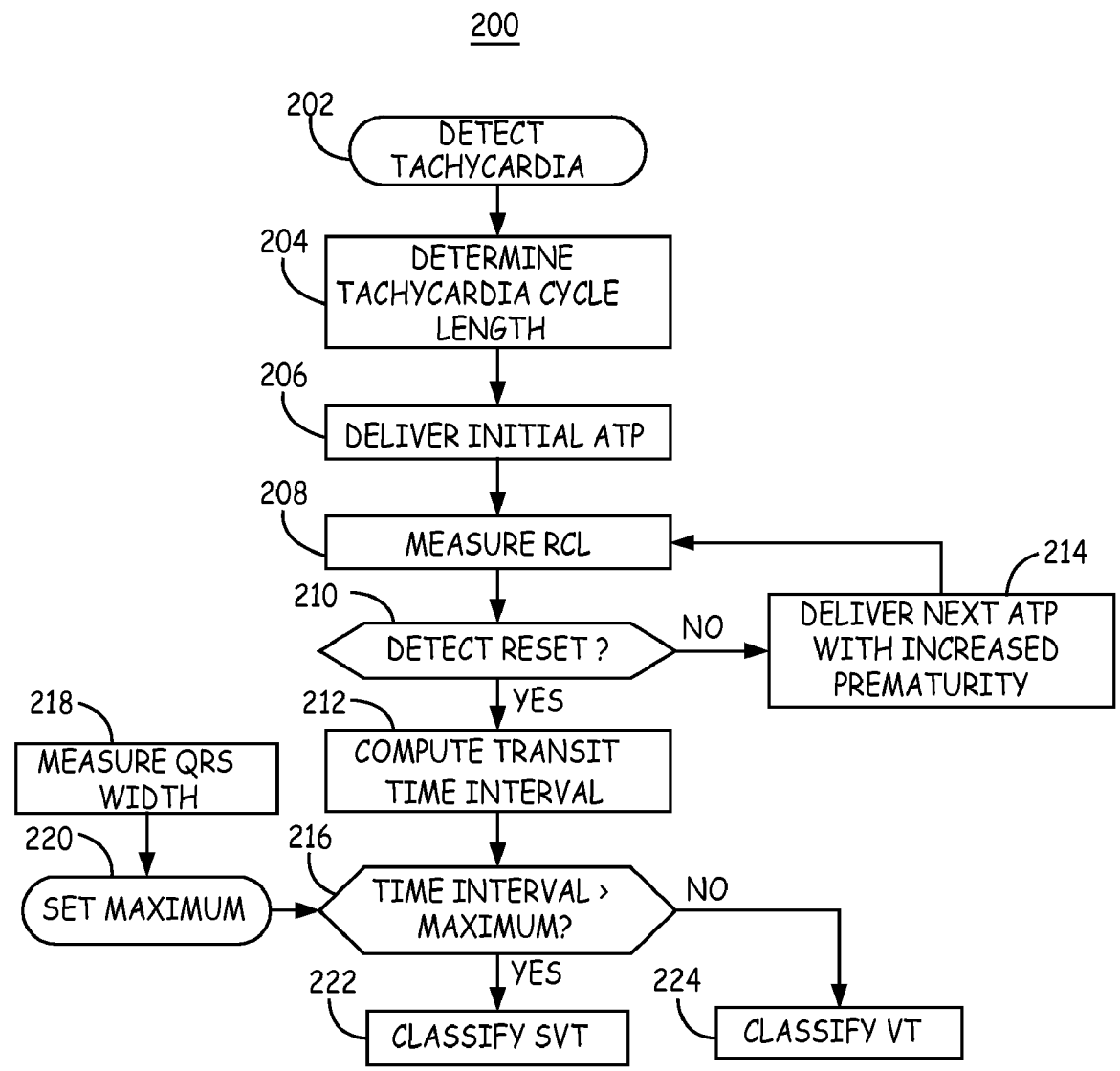
FIG. 8 is a flow chart of one method for discriminating VT and SVT.

FIG. 8 is a flow chart 200 of one method for discriminating VT and SVT based on the concepts described above. Flow chart 200 is intended to illustrate the functional operation of the medical device, and should not be construed as reflective of a specific form of software, hardware or firmware necessary to practice the methods described. It is believed that the particular form of software, hardware and/or firmware will be determined primarily by the particular system architecture employed in the device and by the particular detection and therapy delivery methodologies employed by the device. Providing software, hardware and firmware to accomplish the described functionality in the context of any modern PCD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 202, a tachycardia event is detected. Tachycardia detection may be performed according to any detection algorithm and may be detected using any available sensing electrodes. At block 204, the TCL is measured to determine pacing cycle lengths for an ATP regimen such that the ATP pulses are delivered at cycle lengths that are shorter than the TCL.

At block 206, an initial ATP therapy is delivered. The number of pulses and the total prematurity of the initial ATP regimen may be delivered according to any programmed settings, e.g. according to a first level of therapy in a tiered menu of therapies. As mentioned previously, the initial ATP therapy may be a burst, ramp, ramp plus burst or any other ATP regimen.

Following the last pulse of the ATP therapy, the RCL is measured at block 208. At block 210, the RCL is analyzed to determine if reset is detected. If the RCL is less than the TCL plus the total prematurity of the delivered ATP pulses, reset is detected. If the RCL is approximately equal to (within predetermined uncertainty limits) or greater than the sum of the total prematurity plus the TCL, non-reset is detected. Uncertainty limits may take into account a known or unknown variation in the TCL and may be defined as a percentage of the sum. If non-reset is detected, another ATP regimen is delivered at block 214 with a greater total prematurity than the initial ATP regimen.

Once reset is detected, a time interval corresponding to the distance between the stimulating electrode and the tachycardia origin is computed at block 212 using one of equations 2 or 3 above. If the computed time interval exceeds a predetermined maximum threshold, as determined at block 216, the tachycardia is classified as SVT at block 222. If the computed time interval is less than the threshold, the tachycardia is classified as VT at block 224.

The maximum threshold is set at block 220 and stored in memory. The maximum threshold corresponds to a maximum possible distance from the electrode to a site of origin that is still in the ventricle. If the time interval computed at block 220 as a metric of the distance to the tachycardia origin is greater than the maximum possible distance to any ventricular origin, the tachycardia origin is concluded to be in the atria and the tachycardia event is classified as SVT. The maximum threshold may be tailored according to individual patient need.

The maximum threshold may be based on measurements of an evoked response signal width following a pacing pulse. In the case of a ventricular ATP therapy, the width of a QRS signal may be used for setting a maximum threshold as indicated at block 218. Since the ventricular myocardial mass is largely depolarized by the end of a QRS complex, the QRS width produced by a pacing pulse delivered by the same electrode used for ATP delivery may be used as measure of the time that would be required for a depolarization wavefront to travel from the pacing electrode to any tachycardia site of origin in the ventricles. In one embodiment the maximum threshold is set based on a measured QRS width, e.g., twice the measured QRS width when equation {3} above is used to compute the time interval at block 210. The maximum threshold may be set as a function of the QRS width, such as a fraction or percentage of the QRS width. The QRS width may be measured for the last evoked depolarization from the final pacing pulse of the initial ATP regimen. In atrial ATP applications, an evoked P-wave width may be measured and used for setting a maximum threshold for discriminating SVT and VT.

In alternative embodiments, the maximum threshold may be based on electrophysiological measurements of conduction times taken in an individual patient or a patient population. For example, a conduction time between a ventricular pacing pulse and a subsequent depolarization in the atrium during retrograde conduction may be measured. Alternatively, a conduction time may be measured at the ventricular outflow tract following a ventricular pacing pulse. A measured conduction time can be used to set a maximum threshold corresponding to maximum possible distance from a ventricular electrode delivering an ATP regimen to any ventricular site of origin of a tachycardia.

The comparison of the computed time interval to the maximum threshold at block 216 requires that reset has occurred such that the computed time interval corresponds to the distance to the tachycardia origin and not some intermediate location associated with incomplete peel back. If reset is not detected at block 212, another ATP regimen may be delivered with increased total prematurity in order achieve reset.

Figure 9:
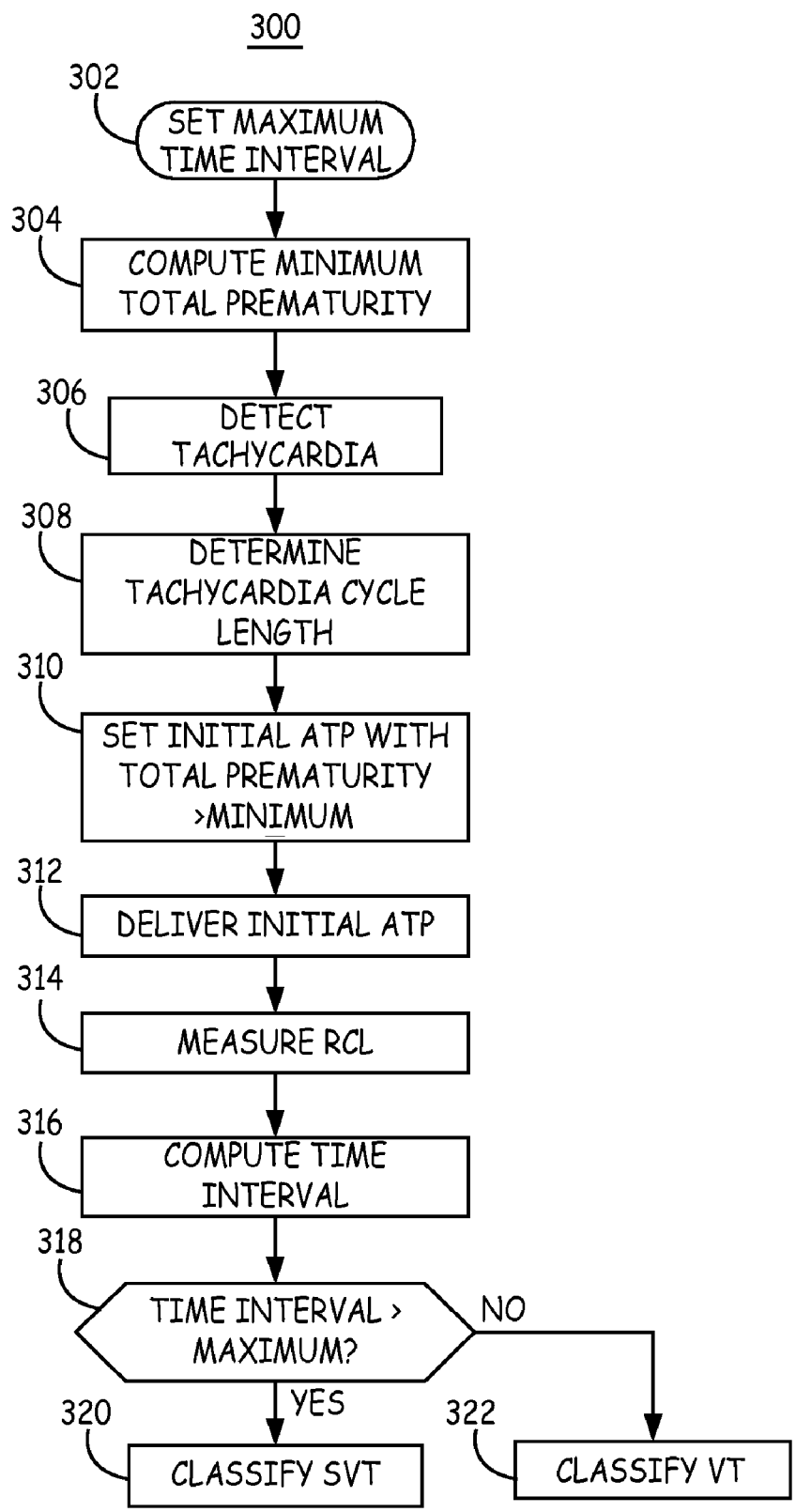
FIG. 9 is a flow chart of an alternative method for classifying a detected tachycardia event.

FIG. 9 is a flow chart 300 of an alternative method for classifying a detected tachycardia event. At block 302, a maximum time interval threshold is set for discriminating SVT from VT. As described above, the maximum threshold may be set according to individual patient need and may include measuring a QRS width and/or using electrophysiology measurements.

At block 304, a minimum total prematurity is computed using the maximum threshold. For example, if a maximum time interval corresponding to a maximum possible distance between an electrode and a ventricular site of origin is set at 180 ms, then the minimum total prematurity of an ATP regimen required to reach a ventricular site of origin can be computed as twice the maximum time interval.

When a tachycardia is detected at block 306, the TCL is measured at block 308. At block 310, the initial ATP regimen is selected taking into account the TCL and having a total prematurity of at least the minimum prematurity computed at block 304. For example, if a burst ATP therapy is selected, the ATP cycle length is selected to be x ms shorter than the TCL. The total number n of pulses in the ATP regimen is selected such that n pulses each delivered at x ms prematurity have a total prematurity (n*x) of at least the minimum total prematurity determined at block 304.

The IMD control processor may compute other ATP regimens, such as ramp or ramp plus burst regimens, that meet the requirement of each ATP cycle length being less than the TCL and the TP of the regimen being greater than the minimum total prematurity computed at block 304. The IMD control processor may thus generate a customized ATP regimen "on-the-fly" based on a measured TCL and a computed minimum TP.

The initial ATP therapy is delivered at block 312. The RCL is measured at block 314. A time interval corresponding to the distance traversed by the final ATP pulse from the electrode is computed at block 316 using the difference between the measured RCL and the measured TCL, e.g., according to equation {3} above. If the time interval exceeds the maximum threshold as determined at block 318, the tachycardia is classified as SVT at block 320. If the computed time interval does not exceed the maximum threshold, the tachycardia is classified as VT at block 322.

Since the total prematurity was computed to ensure reset if the tachycardia origin is within the ventricles, only a single ATP regimen needs to be delivered for rhythm classification. If the computed time interval exceeds the maximum threshold, whether peel back was complete or incomplete, the tachycardia is concluded to be SVT. The last ATP depolarization traveled a distance from the ventricular electrode that would be greater than any possible ventricular site of origin of the tachycardia.

Figure 10:
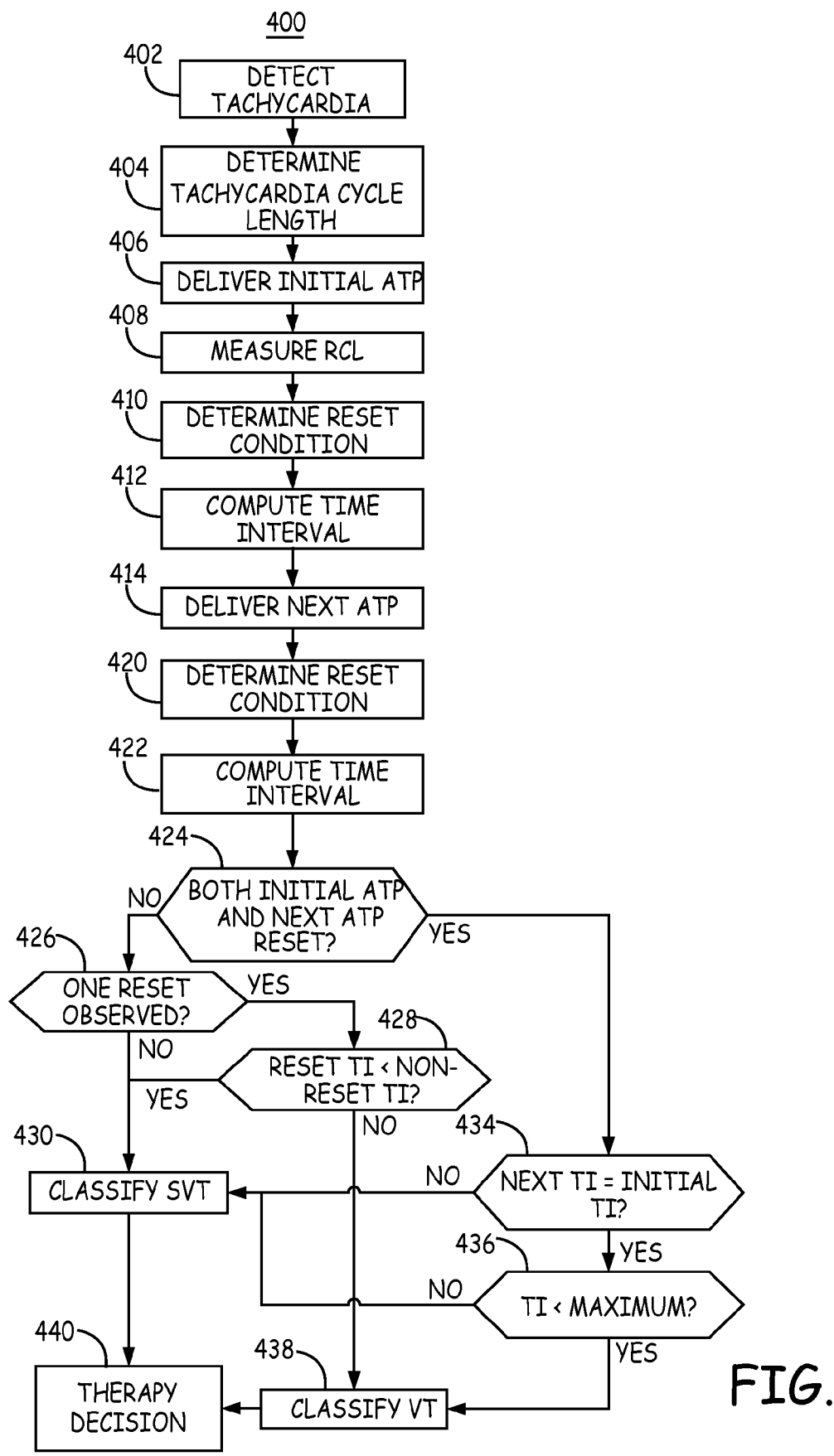
FIG. 10 is a flow chart of yet another method for classifying a detected tachycardia event.

FIG. 10 is a flow chart 400 of yet another method for classifying a detected tachycardia event. Method 400 examines variability in detecting reset or variability in a computed time interval. Inconsistent time intervals or variation between reset and non-reset in response to ATP regimens (e.g., which have a total prematurity of at least twice a maximum threshold or are greater than a measured transit time) are evidence of a tachyarrhythmia origin outside of the paced chamber. When pacing in a chamber not of the tachycardia origin (e.g., pacing in the ventricle during SVT), the return tachycardia wavefront must traverse the cardiac conduction system between atrial and ventricular chambers. Because this conduction system has different refractory properties, there can be a block of the wavefront in the atrial-ventricular conduction system. This conduction block often appears as a non-reset response but may also appear as a reset response that cannot be consistently evoked even though a transit time measured for a reset response indicates that different regimens have a total prematurity that should successfully evoke a reset response.

At block 402 a tachycardia event is detected. The TCL is measured at block 404 and an initial ATP regimen is delivered at block 406. The initial ATP regimen may be set to have a minimum total prematurity required to reach a maximum distance to a ventricular site of origin of the tachycardia as described above in conjunction with FIG. 9. Alternatively, an ATP regimen may be repeated with increasing total prematurity until reset is detected as generally described in conjunction with FIG. 8. For the later option, the total prematurity may be adjusted up to a maximum corresponding to the maximum distance to a ventricular site of origin.

At block 408, the RCL is measured and the reset condition is determined based on the measured RCL as either reset or non-reset at block 410. As described above, the RCL must be less than the total prematurity plus the TCL, in order to detect reset. At block 412, a time interval is computed by determining the difference between the RCL and the TCL. The computed time interval will be the transit time to the tachycardia site of origin in the case of reset. The computed time interval will be a lower bound of the transit time to the tachycardia site of origin if non-reset was detected. In other words, in case of non-reset, the transit time to the tachycardia origin is known to be greater than the computed time interval.

If tachycardia is still detected after the initial ATP and has not accelerated, another ATP regimen is delivered at block 414. The next ATP regimen is delivered and may be the same sequence as the initial ATP or an alternate regimen. The next ATP regimen may have a different total prematurity than the initial ATP, which may be more or less than the initial ATP. In some embodiments, the next ATP regimen has a total prematurity less than the initial regimen but greater than a minimum total prematurity based on a maximum threshold.

The response to the initial ATP and the next ATP regimens will be compared. The efficiency of method 400 may be maximized when the response to the initial ATP is tested by the next ATP regimen. For example, a reset response to an initial ATP with a transit time interval calculated as 90 ms could be followed by an ATP regimen having a total prematurity of at least 90 ms but less than the initial ATP total prematurity. If the same reset response and time interval are not measured following the next ATP regimen, the distance to the tachycardia origin is inconsistent and this inconsistency can be used in discriminating the tachycardia origin.

After the next ATP regimen, the RCL is again measured to allow the reset condition to be determined at block 420. A time interval for the next ATP regimen is computed at block 422 by computing a difference between the RCL and the TCL.

The reset condition determined after the initial ATP and the reset condition determined after the next ATP are compared at block 424. If both the initial and next ATP regimens produced a reset, and the time intervals computed at blocks 412 and 422 are approximately equal (i.e., within an acceptable range of each other) as determined at decision block 434 and at least one is less than the maximum threshold (block 436), the tachycardia is classified as VT at block 438. Approximately consistent time intervals less than the maximum threshold measured when reset is consistently determined is evidence of VT.

If the initial time interval and the next time interval are determined to be significantly different (block 434), or both computed time intervals are not less than the maximum threshold (block 436), the tachycardia is classified as SVT at block 430.

If reset was not observed for both the initial and the next ATP (block 424), and if both reset conditions are determined to be non-reset (block 426), the tachycardia is classified as SVT at block 430. This classification is supported by the fact the initial ATP delivered at block 406 was selected to have a total prematurity corresponding to at least the maximum threshold.

If one reset is observed and one non-reset is observed as determined at block 426, and the reset is associated with a time interval less than the non-reset time interval, as determined at block 428, the tachycardia is classified as SVT at block 430. If the reset time interval is approximately equal to or greater than the non-reset time interval (block 428), the tachycardia is classified as VT at block 438.

Upon appropriately classifying the tachycardia, the PCD processor can control therapy delivery decisions at block 440. Therapy delivery decisions may include continuing a menu of tiered therapies, canceling the therapy, advancing to a more aggressive ATP therapy, changing the chamber in which the ATP therapy is being delivered, or delivering a cardioversion shock. By correctly classifying the tachycardia event, the PCD is able to select a therapy that is most likely to successfully terminate the tachycardia event or to avoid treating a non-lethal tachycardia (such as sinus tachycardia) and prevent serious consequences to the patient.

The method 400 described in FIG. 10 can be extended to include more than two ATP therapy attempts depending on the degree of confidence desired in the tachycardia classification result and the potential impact of additional analysis time on patient outcome. For example, if the overall tachycardia rate is slow (e.g., 150 bpm), multiple ATP therapy sequences for classifying the rhythm may be appropriate. Multiple ATP sequences may be delivered to identify conflicting responses to ATP regimens, e.g., inconsistent reset conditions for the same total prematurity, for different total prematurities each exceeding at least a minimum total prematurity computed using a maximum threshold, or for different total prematurities greater than or equal to a measured transit time from a reset response. Multiple ATP sequences may also result in significantly different time intervals, or a transit time corresponding to reset being shorter than a transit time lower bound established by a non-reset time interval. These conflicting responses to multiple ATP sequences are indicators of SVT when the ATP therapies are delivered in the ventricle. Logical interpretation of inconsistent ATP therapy responses based on cardiac physiology can be applied to appropriately classify a detected tachycardia. For example, inconsistent transit times can be caused by conduction block between the atria and the ventricles and would not be observed when the rhythm origin is in the ventricle and ATP is being delivered in the ventricle. The classification of VT can be made more rigorous in FIG. 10 by requiring two or more reset responses to be observed with consistent transit time intervals before classifying the rhythm as VT.

Thus, a medical device and associated methods for tachycardia discrimination have been presented in the foregoing description with reference to specific embodiments. It is appreciated that various modifications to the referenced embodiments may be made without departing from the scope of the invention as set forth in the following claims.

The invention claimed is:

1. A method, comprising;
sensing cardiac signals and detecting a tachycardia event in response to the sensed cardiac signals;
delivering a first plurality of pacing pulses to a cardiac chamber in response to the detected tachycardia event;
measuring a return cycle length occurring subsequent to the delivery of a last one of the first plurality of pacing pulses;
determining a time interval using the return cycle length, the time interval corresponding to a distance traversed by a depolarization associated with the last one of the first plurality of pacing pulses from a site of delivery of the plurality of pacing pulses; and
classifying the tachycardia event according to a site of origin in response to the determined time interval.

2. The method of claim 1, further comprising:
  determining a maximum time interval for a tachycardia site of origin corresponding to the cardiac chamber;
  comparing the time interval to the maximum time interval; and
  classifying the tachycardia event in response to the comparison.

3. The method of claim 2, wherein determining the maximum time interval comprises measuring a pacing evoked response width.

4. The method of claim 2, wherein determining the maximum time comprises measuring a cardiac conduction time.

5. The method of claim 2 further comprising:
  determining a total prematurity corresponding to the maximum time interval;
  measuring a tachycardia cycle length;
  computing a pacing pulse sequence having pacing pulse cycle lengths less than the tachycardia cycle length and the total prematurity corresponding to the maximum time interval; and
  delivering the first plurality of pacing pulses according to the computed pacing pulse sequence.

6. The method of claim 1 further comprising detecting a first reset condition of the detected tachycardia event in response to the measured return cycle length.

7. The method of claim 6 wherein detecting the reset condition comprises:
  measuring a tachycardia cycle length in response to the detected tachycardia event;
  computing a total prematurity of the first plurality of pacing pulses; and
  detecting reset when the return cycle length is less than a sum of the tachycardia cycle length and the total prematurity.

8. The method of claim 6 further comprising delivering a next plurality of pacing pulses in response to reset not being detected, the next plurality of pacing pulses having a greater total prematurity than a total prematurity of the first plurality of pacing pulses.

9. The method of claim 6 further comprising:
  delivering a next plurality of pacing pulses;
  detecting a next reset condition in response to the next plurality of pacing pulses;
  comparing the next reset condition to the first reset condition; and
  classifying the tachycardia event in response to comparing the reset conditions.

10. The method of claim 6 further comprising:
  delivering a next plurality of pacing pulses;
  determining a next time interval corresponding to a distance traversed by a depolarization associated with the last one of the next plurality of pacing pulses from a site of delivery of the plurality of pacing pulses;
  comparing the time interval and the next time interval; and
  classifying the tachycardia event in response to comparing the time interval and the next time interval.

11. An implantable medical device, comprising:
  an electrode to sense cardiac signals and to deliver a therapy in a cardiac chamber, the therapy comprising a first plurality of pacing pulses;
  sensing circuitry electrically coupled to the electrode to detect a tachycardia event in response to the sensed cardiac signals;
  a processor to control delivery of the therapy, the processor delivering via the electrode the first plurality of pacing pulses in response to the detected tachycardia event; measuring a return cycle length occurring subsequent to the delivery of a last one of the first plurality of pacing pulses; determining a time interval using the return cycle length, the time interval corresponding to a distance traversed by a depolarization associated with the last one of the plurality of pacing pulses from a site of delivery of the plurality of pacing pulses; and classifying the tachycardia event according to a site of origin in response to the determined time interval.

12. An implantable medical device, comprising:
  means for sensing cardiac signals and delivering a therapy in a cardiac chamber, the therapy comprising a first plurality of pacing pulses;
  means for detecting a tachycardia event in response to the sensed cardiac signals; and
    means for controlling delivery of the therapy, the means for controlling delivery comprising:
    means for delivering the first plurality of pacing pulses via the electrode in response to the detected tachycardia event;
    means for measuring a return cycle length occurring subsequent to the delivery of a last one of the first plurality of pacing pulses;
    means for determining a time interval using the return cycle length, the time interval corresponding to a distance traversed by a depolarization associated with the last one of the plurality of pacing pulses from a site of delivery of the plurality of pacing pulses;
    means for classifying the tachycardia event according to a site of origin in response to the determined time interval;
    means for determining a maximum time interval for a tachycardia site of origin corresponding to the cardiac chamber;
    means for comparing the time interval to the maximum time interval; and
    means for classifying the tachycardia event in response to the comparison.

13. The device of claim 12, wherein the means for controlling delivery of the therapy measures a pacing evoked response signal width and determines the maximum time interval in response to the measured evoked response signal width.

14. The device of claim 12 wherein the means for controlling delivery of the therapy measures a cardiac conduction time and determines the maximum time interval in response to the measured conduction time.

15. The device of claim 12 wherein the means for controlling delivery of the therapy further comprises:
  means for determining a total prematurity corresponding to the maximum time interval;
  means for measuring a tachycardia cycle length;
  means for computing a pacing pulse sequence having pacing pulse cycle lengths less than the tachycardia cycle length and the total prematurity corresponding to the maximum time interval; and
  means for delivering the first plurality of pacing pulses according to the computed pacing pulse sequence.

16. An implantable medical device, comprising:
  means for sensing cardiac signals and delivering a therapy in a cardiac chamber, the therapy comprising a first plurality of pacing pulses;
  means for detecting a tachycardia event in response to the sensed cardiac signals; and means for controlling delivery of the therapy, the means for controlling delivery comprising:

means for delivering the first plurality of pacing pulses via the electrode in response to the detected tachycardia event;

means for measuring a return cycle length occurring subsequent to the delivery of a last one of the first plurality of pacing pulses;

means for determining a time interval using the return cycle length, the time interval corresponding to a distance traversed by a depolarization associated with the last one of the plurality of pacing pulses from a site of delivery of the plurality of pacing pulses;

means for classifying the tachycardia event according to a site of origin in response to the determined time interval; and means for detecting a first reset condition of the detected tachycardia event in response to the determined return cycle length.

17. The device of claim 16 wherein the means for detecting a first reset condition comprises:

means for measuring a tachycardia cycle length in response to the detected tachycardia event;

means for computing a total prematurity of the first plurality of pacing pulses; and means for detecting reset when the return cycle length is less than a sum of the tachycardia cycle length and the total prematurity.

18. The device of claim 16 wherein the means for controlling delivery of the therapy delivers, via the electrode, a next plurality of pacing pulses in response to reset not being detected, the next plurality of pacing pulses having a greater total prematurity than a total prematurity of the first plurality of pacing pulses.

19. The device of claim 16 wherein the means for controlling delivery of the therapy further comprises:

means for delivering a next plurality of pacing pulses via the electrode;

means for determining a next time interval corresponding to a distance traversed by a depolarization associated with the last one of the next plurality of pacing pulses from a site of delivery of the plurality of pacing pulses;

means for comparing the time interval and the next time interval; and means for classifying the tachycardia event in response to the comparison of the time interval and the next time interval.

20. A computer readable medium storing a set of instructions which when implemented in an implantable medical device system cause the system to:

sense cardiac signals and detecting a tachycardia event in response to the sensed cardiac signals;

deliver a first plurality of pacing pulses in a cardiac chamber in response to the detected tachycardia event;

measure a return cycle length occurring subsequent to the delivery of a last one of the first plurality of pacing pulses;

determine a time interval using the return cycle length, the time interval corresponding to a distance traversed by a depolarization associated with the last one of the first plurality of pacing pulses from a site of delivery of the plurality of pacing pulses; and classify the tachycardia event according to a site of origin in response to the determined time interval.

* * * * *